(12) United States Patent
Benedetti et al.

(10) Patent No.: US 7,173,246 B2
(45) Date of Patent: Feb. 6, 2007

(54) PORTABLE APPARATUS FOR THE NON-DESTRUCTIVE MEASUREMENT OF THE INTERNAL QUALITY OF VEGETABLE PRODUCTS

(76) Inventors: Angelo Benedetti, Via Basilica, 166, I-48020 Savarna (IT); Ezio Pasini, Via Di Vittorio 19, I-48011 Alfonsine (IT); Franco Forlani, Via Namibia 3, I-44015 Portomaggiore (IT); Luca Montanari, Via Savarna, 233/B, I-48020 Savarna (IT)

( * ) Notice: Subject to any disclaimer, the term of this patent is extended or adjusted under 35 U.S.C. 154(b) by 246 days.

(21) Appl. No.: 10/475,106

(22) PCT Filed: Feb. 22, 2002

(86) PCT No.: PCT/EP02/01872

§ 371 (c)(1),
(2), (4) Date: Oct. 17, 2003

(87) PCT Pub. No.: WO02/088678

PCT Pub. Date: Nov. 7, 2002

(65) Prior Publication Data
US 2004/0149916 A1 Aug. 5, 2004

(30) Foreign Application Priority Data
Apr. 27, 2001 (IT) .......................... PN2001A0032

(51) Int. Cl.
*G01J 1/06* (2006.01)

(52) U.S. Cl. .................................................. 250/358.1

(58) Field of Classification Search ............. 250/358.1, 250/359.1; 356/73, 419
See application file for complete search history.

(56) References Cited

U.S. PATENT DOCUMENTS

| 3,910,701 | A | * | 10/1975 | Henderson et al. | ........... 356/39 |
| 5,013,155 | A | * | 5/1991 | Rybak | ......................... 356/408 |
| 5,708,271 | A | | 1/1998 | Ito et al. | |
| 5,729,640 | A | * | 3/1998 | Castonguay | ................ 382/321 |
| 6,014,222 | A | * | 1/2000 | Borggaard et al. | .......... 356/419 |

(Continued)

FOREIGN PATENT DOCUMENTS

EP 0939316 A2 9/1999

(Continued)

*Primary Examiner*—Otilia Gabor
(74) *Attorney, Agent, or Firm*—Wenderoth, Lind & Ponack, L.L.P.

(57) ABSTRACT

An apparatus for non-destructive measurement of internal properties of individual vegetable or fruit pieces comprises: LEDs constructed and arranged to emit radiation into a vegetable or fruit product; pick-up structure constructed and arranged to pick up radiation, emitted by the LEDs, that has entered the vegetable or fruit product and then exited the vegetable or fruit product; a hollow cylinder between the LEDs and the pick-up structure for preventing radiation emitted by the LEDs from directly reaching the pick-up structure; a spectrometer; structure for conveying to the spectrometer the radiation picked up by the pick-up structure; and structure for processing a spectrum frequency and amplitude data as produced by the spectrometer upon the radiation picked up by the pick-up structure being analyzed by the spectrometer.

17 Claims, 8 Drawing Sheets

U.S. PATENT DOCUMENTS

| | | | |
|---|---|---|---|
| 6,122,042 A * | 9/2000 | Wunderman et al. | 356/73 |
| 6,246,479 B1 * | 6/2001 | Jung et al. | 356/419 |
| 6,590,660 B2 * | 7/2003 | Jung et al. | 356/419 |
| 2005/0010090 A1 * | 1/2005 | Acosta et al. | 600/316 |
| 2005/0020892 A1 * | 1/2005 | Acosta et al. | 600/316 |

FOREIGN PATENT DOCUMENTS

| | | |
|---|---|---|
| JP | 5-288674 | 11/1993 |
| JP | 2000-88747 | 3/2000 |
| WO | 00/13808 | 3/2000 |

* cited by examiner

PORTABLE APPARATUS FOR THE NON-DESTRUCTIVE MEASUREMENT OF THE INTERNAL QUALITY OF VEGETABLE PRODUCTS

The present invention refers to a portable apparatus for measurement of a value of some internal substances and properties of vegetable or fruit products, in particular individual items of any fruit or vegetable variety whatsoever, with the internal substances and properties being adapted to be indicative of, i.e. reveal, an internal "quality" of the product being measured.

Fruit is largely known to be usually picked off and then selected, i.e. graded, through a process that is based on a variety of judgments, inspections and examinations, insofar as not only a correct time for picking, which should ideally occur when characteristics of products to be picked are at an optimum altogether, but also a kind of inspections and controls are concerned, which must be performed on most significant properties of each single fruit item in order to evaluate most important characteristics in view of grading quality and, therefore, determining a final commercial destination thereof.

However, since an ideal time for picking fruit can most obviously be only identified when the fruit is actually still ripening and, therefore, still on a tree (being it actually possible, but quite risky to pick off fruit and examine it only afterwards to find out that it has been picked too early), a need arises, for a correct selection of a most favorable time for picking, for the inspections and controls to be able to be performed on the fruit items before picking them off, i.e. when they are still on the tree.

However, since vegetable and fruit products are natural products, they possess characteristics that may be non-uniform, i.e. may change from one piece of fruit to a next one, and this fact does not enable quality and a ripening state of each single fruit item to be merely assessed on a basis of a simple sample test to be performed on a limited number of fruit items that have been previously picked off a tree.

Furthermore, an assessment of a ripening state of fruit depends on a number of parameters, such as mainly sugar contents, acidity, water contents and hardness. However, a factor that actually makes it particularly difficult for a suitable instrument to be implemented and a single procedure to be adopted for measuring a degree of ripening of vegetable products, is that each single species thereof has its own peculiar characteristics of a ripe product, which may often be also quite different from similar characteristics of an equally ripe product that belongs to a different species. All this is well known to all those skilled in the art, so that it shall not be dealt with here any further, in the same way as a large number of examples that can be given here in this connection shall be omitted for reasons of greater simplicity.

It is therefore an obvious and easily understandable fact that a search for a measurement apparatus and related procedure for measuring a degree of ripeness in general of vegetable or fruit products has split up into a rather high number of technical solutions in connection with both a variety of technical investigation devices used (such as, for example, laser beams, quartz-iodine or halogen light, advanced statistical processing methods) and concepts of implementation of specialized measurement apparatuses/instruments for each single species of products to be measured.

In general, a state of the art in the field of not only measurement of some significant properties of vegetable products both during and after picking, but also methods of processing data issuing from these measurements and related measuring and processing apparatuses/instruments, are collected in the bibliography listed in enclosed Table1 (sheets 1 and 2).

A number of instruments and apparatuses are therefore largely known in the art for measuring in an automatic and relatively low-cost manner a value of some of the above cited parameters; to mere documentary evidence purposes following references may be cited in this connection: EP 957353, U.S. Pat. No. 4,473,292, U.S. Pat. No. 5,844,678, U.S. Pat. No. 5,658,798, U.S. Pat. No. 5,708,271. The latter refers in particular to sole control of the Brix degree as performed with a non-portable apparatus.

However, all these apparatuses or instruments are industrial devices intended for application in mass processing of fruit items that have already been picked off a tree, or else are laboratory-scale apparatuses, so that none of them is actually adapted, nor likely to be capable of being adapted, to be used as a portable instrument for testing fruit pieces as they are still hanging on a tree.

U.S. Pat. No. 5,519,219 discloses an apparatus for spectrometric measurement and quantitative identification of solids, liquids and gases, comprising an IR source and an LED-based reading device. This apparatus, however, can examine both solids and liquids or gases, so that it is absolutely not suitable for use to solely measure such special items as individual pieces of fruit.

Patent publications JP 10206323, JP 10160670, JP 08068751 and JP 081288949 disclose technical solutions for analysis of properties of vegetable products through utilization of laser ray beams; however, such a technology is quite delicate and expensive, and does not lend itself to any agile utilization for assessment of qualities of vegetable or fruit products that have not yet been picked.

Patent publication WO 00/02036 refers to a non-portable instrument that has been conceived to solely analyze chlorophyll contents in a vegetable product; such a solution is quite obviously capable of generating information of a considerably limited extent that cannot therefore be reasonably relied upon as far as an assessment of a degree of ripeness of an examined product is concerned.

Patent publication U.S. Pat. No. 5,822,068 covers analysis of vegetable products to be only performed, through examination of luminescence, after such products have been picked. To such a purpose, use is made of both low-intensity and high-intensity red light beams, and this causes such a method to become rather complex and expensive and, therefore, practically unfitted to applications involving controls to be performed in a quick and reliable manner throughout.

Patent publication EP 0939316 discloses a method and an apparatus for measurement of internal characteristics of a fruit item. However, therein disclosed solutions have a major drawback in that they make use of a traditional light source, which therefore is very expensive from an energy usage viewpoint and, as a result, practically non-portable. In addition, a suggested solution provides for a bundle of optical fibers carrying radiation to be placed in contact with a same portion of a fruit surface along with another bundle of optical fibers carrying a feedback, i.e. return radiation. It has however been found that such a solution has a major drawback in that the feedback radiation that is picked up in this way is very low in level and, furthermore, is markedly contaminated by an effect of direct reflection, by the surface of the fruit, of incident radiation. As a result, the radiation that is so obtained in return from the fruit is rather disguised and scarcely capable of being decoded into simple and reliable pieces of information.

Finally, what is actually processed in this case, and hence results that are so worked out, are based on an average of all measurements that are performed, and not on the measurements of each single product, so that they are not fitted for use in view of a punctual evaluation of each product; alternatively, evaluation of a single product requires two distinct measurements to be performed, so that it turns out to be quite demanding and complex in operational terms and, therefore, all the more so scarcely usable in applications involving measurements on products that have not yet been picked.

Known from the disclosure in U.S. Pat. No. 5,324,945 is a method for non-destructive measurement of sugar contents of fruit items; this method, however, is based on a non-portable apparatus and, furthermore, is limited to sole measurement of the sugar contents.

It therefore is desirable, and is actually a main purpose of the present invention to provide a technical solution, and a related instrument, for non-destructive measurement of some internal substances and properties of a vegetable or fruit product, in which the instrument shall further be capable to be conveniently used on fruit items that are still hanging on a tree, i.e. have still to be picked. The instrument shall be conveniently portable and be capable of generating electric signals that are adapted to be appropriately processed so as to provide information that is capable of being correlated with a state of ripeness and a quality of the fruit being examined.

According to the present invention, this aim, along with other features of the present invention, are reached in a portable apparatus that is made and operates as recited in the appended claims.

BRIEF DESCRIPTION OF THE DRAWINGS

Features and advantages of the present invention will be more readily understood from the description that is given below by way of non-limiting example with reference to the accompanying drawings, in which.

DETAILED DESCRIPTION OF THE PREFERRED EMBODIMENTS

Figure 1:
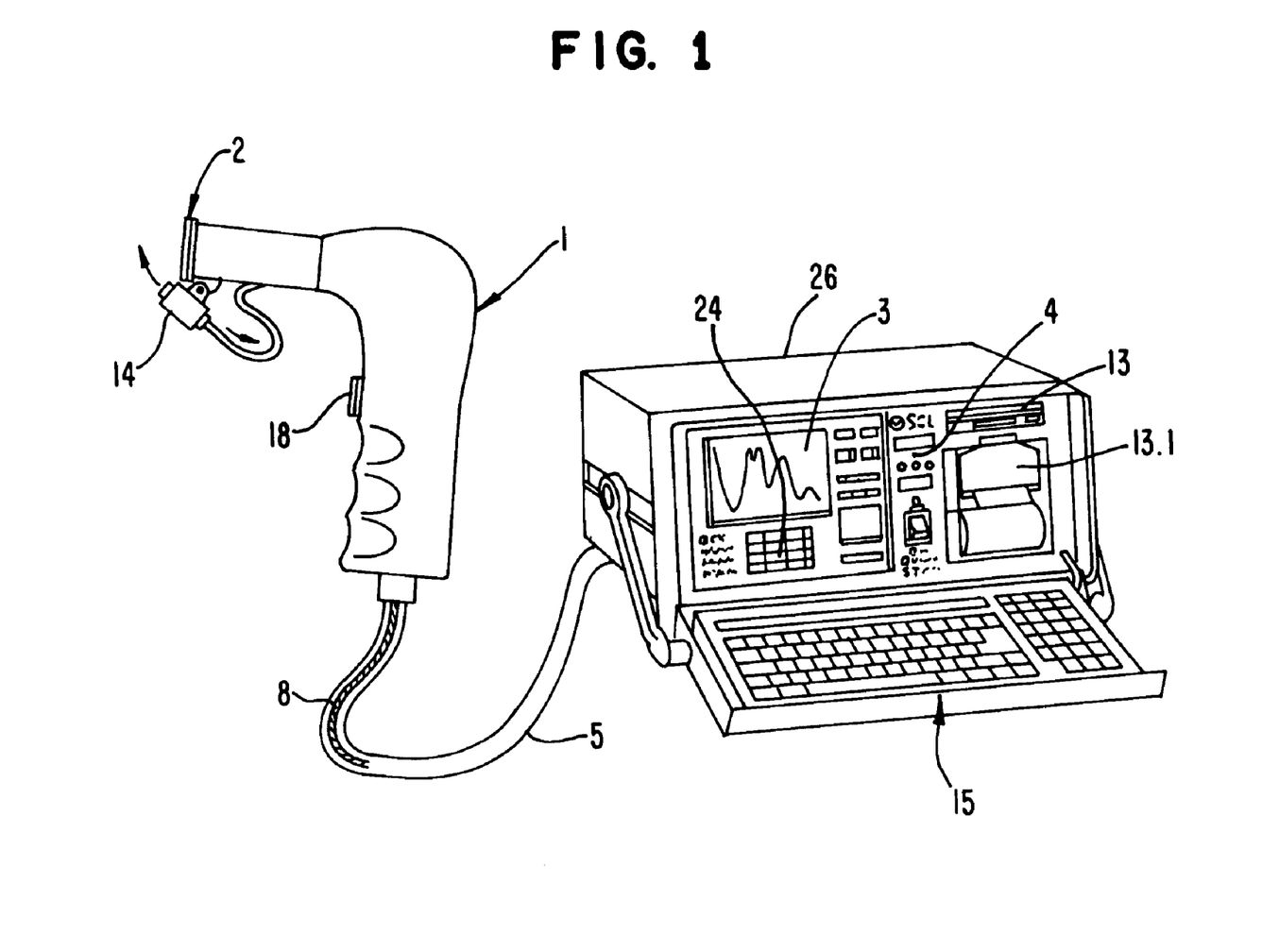
FIG. 1 is a schematic and symbolic view of two assemblies that constitute an instrument according to the present invention.
Figure 2:
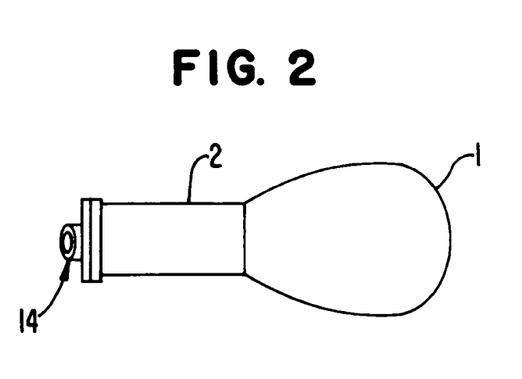
FIG. 2 and FIG. 3 are a top view and a front view, respectively, of a left-hand assembly of FIG. 1.
Figure 3:
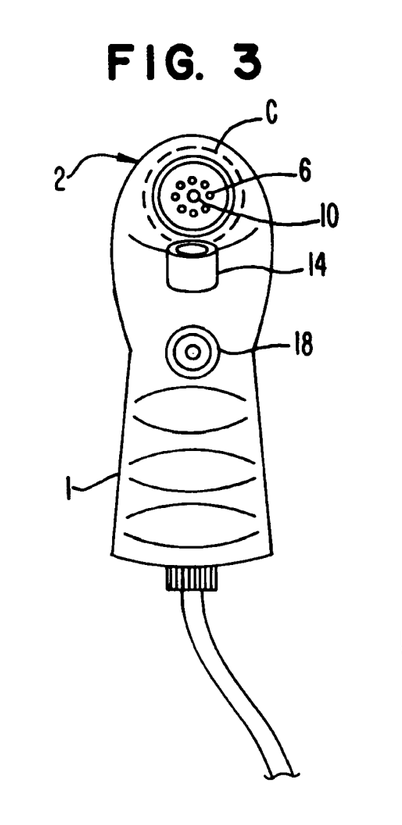

With particular reference to FIG. 1, it can be noticed that an instrument according to an example of an embodiment of the present invention comprises:

a portable structure, preferably in the shape of a handgun, and in any event provided with a handgrip 1 and a probing head 2;

a spectrometer 3 associated with a suitable processing and computing device 4, which is preferably given the same architecture as a personal computer (PC); wherein the spectrometer 3 and the processing and computing device 4 are preferably assembled and integrated inside a single casing 26, which is also portable, so as to ensure full portability of this entire instrument; and a plurality of electric and optical connections, twisted and joined together into a single cable 5, provided between the handgrip 1 and an association between the spectrometer 3 and PC 4.

Figure 5:
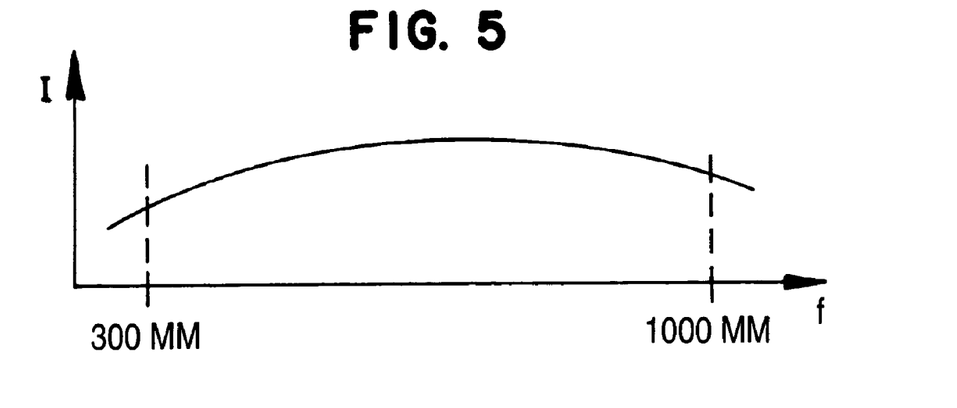
FIG. 5 is a diagrammatic view of an example of light radiation intensity as a function of wavelength of either a traditional or halogen light source.

Some basic teachings of the present invention need at this point to be introduced. According to prior art, instruments and apparatuses are disclosed which generate and emit a light or quasi-light radiation (NIR, Near Infrared Radiation) having quite a wide spectrum (see FIG. 5), i.e. a spectrum that is therefore an ideal one in view of being able to analyze properties and quality of an inner part of vegetable products; however, these apparatuses make use of a light source that comprises either a halogen, i.e. a quartz-iodine lamp, or a traditional lamp. In other words, they use illuminating devices that use a lot of energy.

On the other hand, since it is desired that such devices be capable of being portable, an absolute need arises for these devices to be provided with portable energy sources, i.e. batteries. Owing to these devices implying a rather large energy usage, as stressed above, it would prove necessary to either make use of quite heavy and bulky power-supply batteries, and this would of course affect actual transportability of an apparatus, or drastically limit an operating endurance, or self-sufficiency, and this would of course imply a significant reduction in actual usefulness and advantages in use of the apparatus.

In order to do away with such drawbacks, use is therefore proposed of light sources based on use of LEDs (i.e. Light Emitting Diodes), which have a very low energy usage and, as a result, are capable of being supplied for a long period of time, instead of light-weight and compact-sized batteries.

The probing head 2 of the apparatus according to the present invention comprises:

a plurality of LED devices 6 arranged on an end portion of the probing head;

a pick-up member 7, arranged in close proximity of the LEDs 6 to pick-up light from outside, one or more optical fibers 8, connected to light pick-up member 7 on one side and, on another side, to the spectrometer 3.

Quite logically, there are furthermore provided, although not shown in the figures, circuits that are required to ensure power supply to the LED devices 6.

Figure 4:
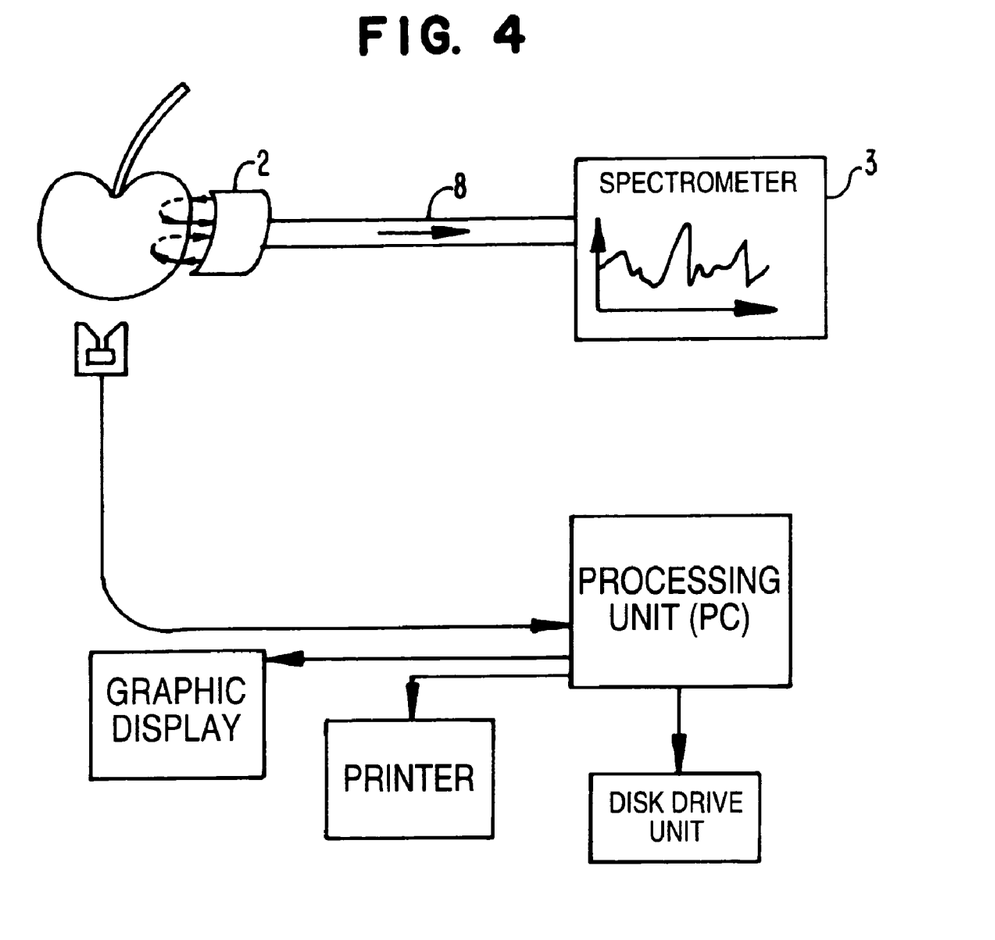
FIG. 4 is a symbolic, schematic view of connections between main functional members of the instrument according to the present invention.

FIG. 4 illustrates a symbolic, simplified block diagram showing various component parts of the apparatus according to the present invention, which will be used further on in this description and is useful in view of better understanding a real object of the invention.

However, each type of the LEDs is capable of emitting light on a very narrow spectrum, in particular a spectrum that is much narrower than a halogen light spectrum.

Such a circumstance gives rise to a severe limitation, since reliability and accuracy of spectrum analysis of return or feedback radiation depends to quite a large extent on amplitude of a spectrum itself.

Figure 6:
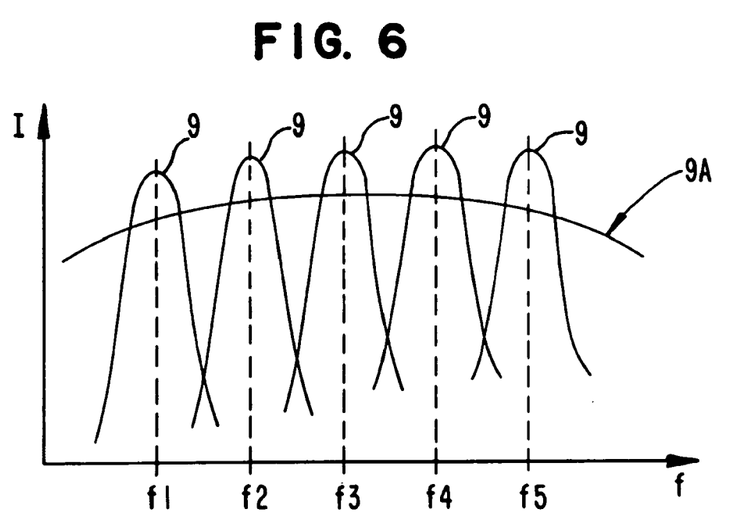
FIG. 6 is a diagrammatic view of a plurality of curves relating to light radiation intensity as a function of wavelength of respective LEDs selected according to the present invention.

In order to remove such a limitation, a plurality of LEDs are actually selected, which have respective differentiated, but substantially contiguous spectra 9, so that in their entirety the LEDs are capable of generating light radiation having an overall spectrum that is approximately as wide as spectrum 9A of a halogen or traditional light source (see FIG. 6).

Light radiation is in this way obtained, which has approximately the same characteristics as halogen light radiation, while however implying an extremely reduced low-voltage energy usage that can therefore be quite well sustained by normal general-purpose portable batteries.

Figure 7:
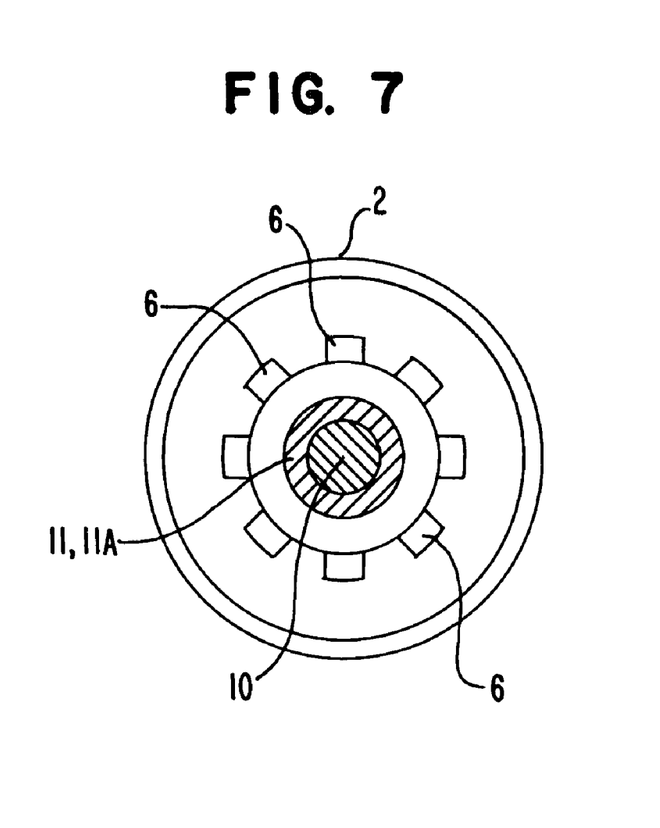
FIG. 7 is an enlarged front view of a portion identified as "C" in FIG. 3.
Figure 8:
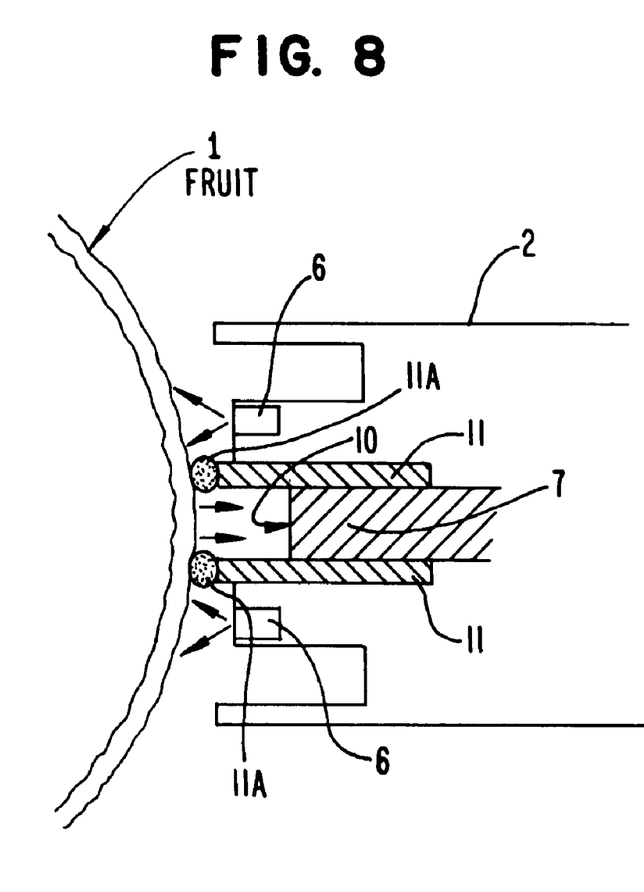
FIG. 8 is a view of the portion identified as "C" in FIG. 3 according to section A—A in FIG. 7.
Figure 9:
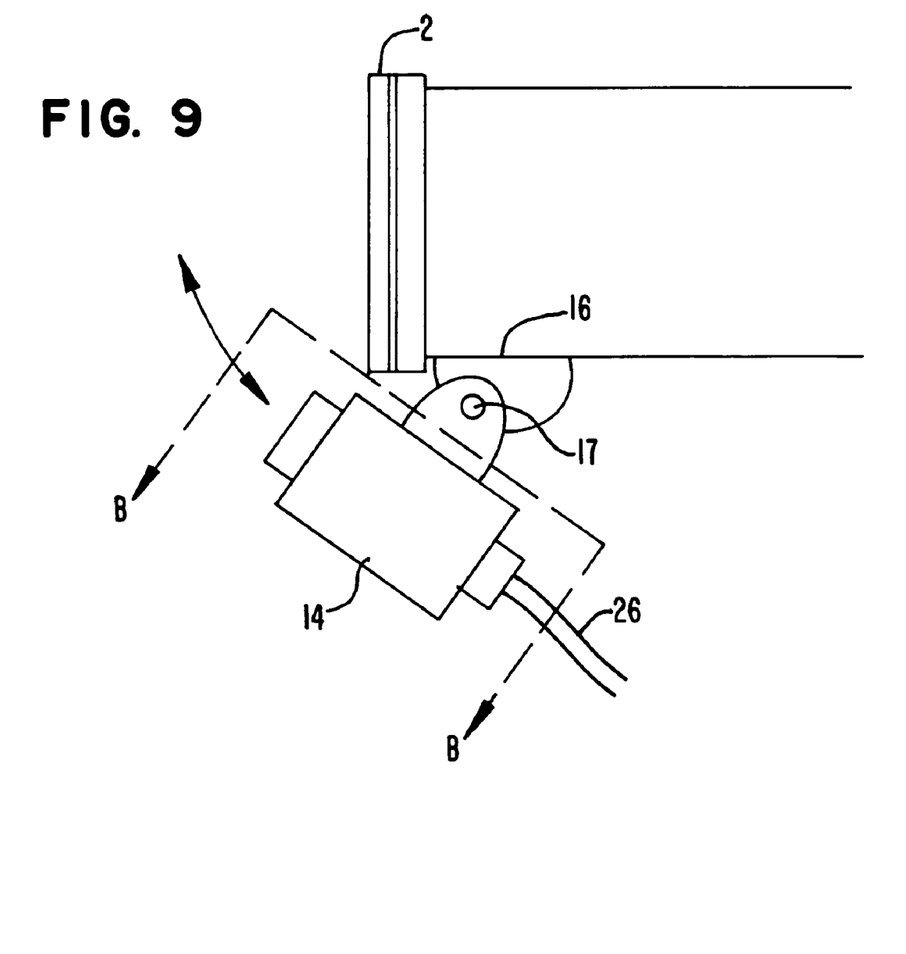
FIG. 9 is an enlarged view of a terminal portion of the left-hand assembly of FIG. 1.
Figure 10:
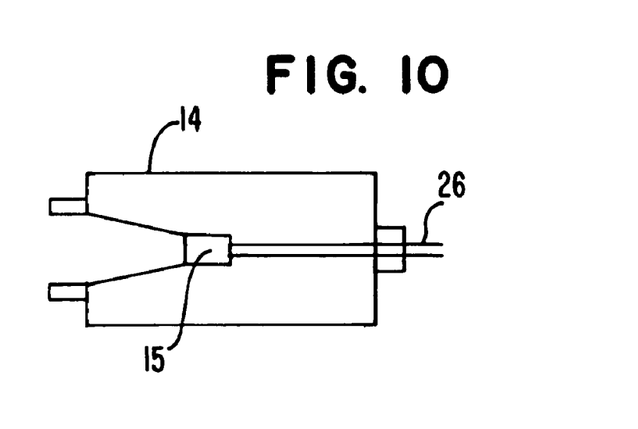
FIG. 10 is a view of a component part of the terminal portion, as seen according to section B—B in FIG. 9.

In an advantageous manner, in view of enabling this so obtained light radiation to uniformly penetrate an item to be examined, as well as light radiation re-emitted outside from the item to be picked up in a manner that is not distorted by a geometry of both a transmission and pick-up device, the LEDs and the light pick-up member 7 are arranged coaxially, and preferably, with reference to FIGS. 7 and 8, the LEDs are arranged according to one or more closed-loop ring patterns, while the light pick-up member 7 is arranged at a center of such closed-loop ring patterns.

The light pick-up member 7 is constituted by an outer surface 10 of a termination of optical fiber 8.

A mode of operation of this part of the instrument according to the present invention is as follows. The probing head 2 is first of all approached to a vegetable or fruit product so as to enable the pick-up member 7 to come into soft contact with a surface of this product to be analyzed; and then, previously energized LEDs emit a corresponding radiation that strikes upon the surface of the product and penetrates the product itself.

Behavior of such radiation is well-known; a part of this radiation in a visible and NIR spectrometric region (400 nm–2500 nm) is partly refracted and scattered into a body of the product from sub-epidermal layers of the product, and then returns towards the surface of the product and, moving beyond a barrier constituted by the peel, gets back to an exterior of the product. In particular, chemical bonds of a determined substance absorb energy associated with specific wavelengths in proportion to concentration of that substance. A possibility is therefore given for concentration of the substance to be determined through measurement of this absorption.

A part of the radiation that moves beyond the peel, and therefore gets back to the exterior of the product (return or feedback radiation), is picked up by the pick-up member 7, and by virtue of one or more optical fibers 8 is transmitted to an appropriate spectrometer for further processing, as this shall be described in greater detail further on.

In order to ensure that the return radiation is not likely to be mixed either with ambient light or radiation being directly emitted by the LEDs, and therefore reaching by diffusion the pick-up member, with reference to FIG. 8 following geometry is selected:

the LEDs 6 are arranged according to a closed-loop ring pattern, and oriented outwards, on a surface of the probing head;

at a center of the closed-loop ring pattern there is arranged the pick-up member 7, which is internally connected with one or more optical fibers 8 and terminates externally with the pick-up surface 10; an internally hollow cylinder 11, preferably of an elastomeric or, similar soft material, is provided between the member 7 and the LEDs 6 and is arranged so as to be slightly projecting with respect to both the member and the LEDs, which therefore are set back with respect thereto and, in particular, are not exposed to view from among each other, i.e. are not visible from each other.

It will therefore be readily appreciated that, when the head 2 is approached to a fruit, a kind of "obscure chamber", or "camera obscura", is created between the fruit and the pick-up member 7, owing to the hollow cylinder 11 being brought to softly rest against a surface of the fruit; in this way, the pick-up member 7 can be reached solely by radiation that comes out of a peel and, therefore, is exactly and accurately representative of an internal state of the fruit, since both ambient light and light emitted by the LEDs are effectively intercepted and fully barred by the hollow cylinder 11.

Advantageously, the hollow cylinder 11 may be accompanied, on its outer circular surface oriented towards the fruit, by a particularly soft terminal ring 11A that is capable of being brought to most softly abut against the fruit (see FIG. 7). As an alternative thereto, the terminal ring 11A may be provided directly on the probing head 2 with aid of proper structure, while thereby avoiding being applied to the hollow cylinder 11, provided of course that a basic condition is duly preserved, i.e. that the pick-up member 7 is capable of being only and solely reached by radiation coming from the peel of the fruit and, therefore, from an inner part of a product being measured.

Radiation that is in this way received by the pick-up member is then sent to the spectrometer, which outputs a graph or a function of an intensity pattern of the return or feedback radiation as a function of frequency of this radiation.

A function supplied by the spectrometer is then processed by the PC according to following criteria:

for each type of program selected, there are associated and filed, i.e. stored, a multiplicity of formulae and/or algorithms that use frequencies and related amplitudes as variables; each formula or algorithm generates a calculation relating to one of the following parameters:

sugar contents (Brix degree)

hardness degree of ripeness acidity residual pesticides;

since in a case described here as an example there are five of the parameters, also the formulae or algorithms will also be five in number;

the PC unit processes and solves the formula on a basis of an amplitude of the return radiation at a certain predefined number of frequencies of the spectrum, and performs a processing operation for all formulae associated with the selected program, thereby obtaining values relating to each one of the above mentioned parameters; and on a basis of values obtained by processing the formulae, the PC unit then outputs information containing the values it has so just computed.

Figure 11:
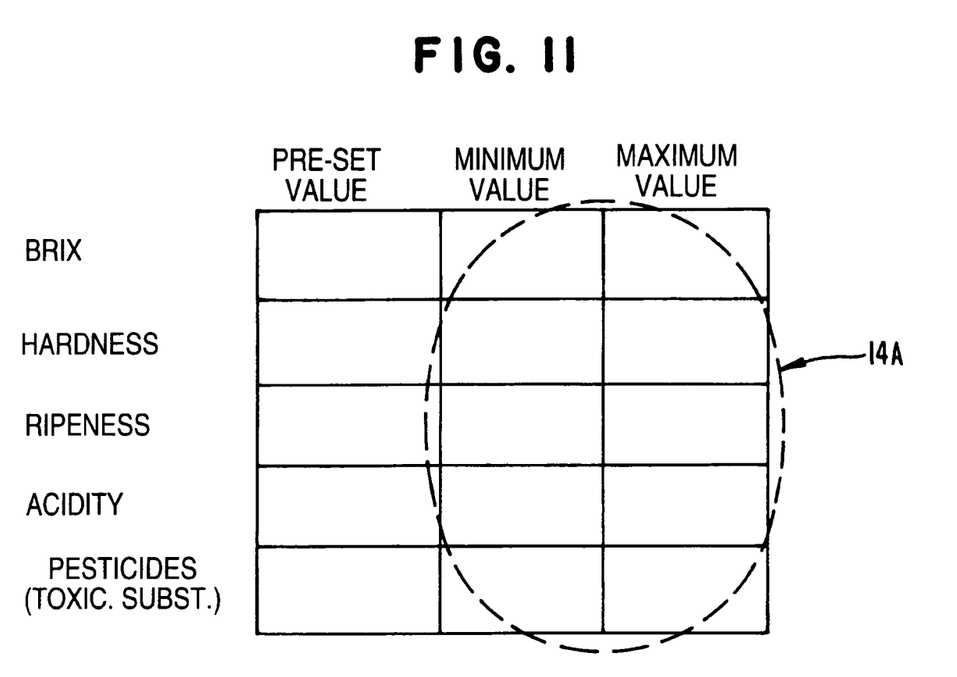
FIG. 11 is an enlarged view of part of a display provided on a right-hand assembly of FIG. 1.

In a suitable manner, such an output information of values that have been processed on the basis of measurement ("predicted" values) occurs in the form of a contemporaneous numerical presentation on a proper display 24; in addition, maximum and minimum values found from an initial, pre-set measurement, or pre-established quality indexes, may also be detected, recognized and stored, and these values may then be presented on a special display 14A (see FIG. 11) for a final evaluation of overall peculiarities of many vegetable or fruit products that have been so analyzed.

It can therefore be readily appreciated that, once a kind of vegetable product to be examined has been identified and a corresponding program has been selected through proper controls on a keyboard of the PC, measurement of characteristics occurs in a very simple, immediate and, above all, fully automatic manner.

It will also be readily appreciated that this PC unit shall first be loaded with a plurality of computational programs, corresponding to various species and conditions of vegetable products to be analyzed, which must be capable of being selectively selected by an operator.

As far as determination of formulae or algorithms, these are obtained by going through a large number of experiments, i.e. measurements of graphs generated by the spectrometer and comparisons with values of cited parameters as measured in a conventional, known manner, including contents and kinds of pesticides that may possibly be present and investigated, i.e. checked for. Results of such comparisons are processed with most appropriate statistical techniques, such as typical multiple regression, designing of fractional factorial experiments, as well as other suitable statistical methods that, however, are not a part of the present invention and shall therefore not be dealt with here any further. Anyway, an outcome of all these processing steps enables a formula or algorithm to be identified, which provides with an adequate and acceptable accuracy a manner for determining, or predicting, a value of a definite parameter that is representative of a corresponding characteristic of an internal quality of a fruit or vegetable, on a basis of a function worked out, i.e. found by the spectrometer.

In an advantageous manner, the spectrometer 3 and the computation device 4 are associated with each other in a single and same assembly, as this is shown in FIG. 1. Associated to such an assembly there are arranged also appropriate peripheral units, such as at least a driver 13 for entering and retrieving data and programs, a display 14 for presentation of values of computed parameters, a printer 13.1 and a keyboard 15 for entering commands.

However, it is a largely known fact that a value of parameters that can be detected or found out with known, conventional techniques is markedly dependent on a temperature of a vegetable product being analyzed; for this reason, when used in determination of formulae/algorithms, reference values that are so found experimentally should be adjusted with help of appropriate correction coefficients relating to a temperature of the vegetable product. However, since these experiments are performed at any prevailing ambient temperature, the corrections, which must be made in order to take into due account an actual temperature of the vegetable or fruit product to be analyzed, are introduced through an appropriate additional processing step of the formulae/algorithms.

A need therefore arises for the temperature of the vegetable or fruit product to be detected and result of such a measurement to be suitably entered in the PC unit, so as to be able to work out computational steps relating to various parameters in such a way as to duly take such a temperature effect into due account.

To this purpose, the probing head 2 is provided with a temperature-detection piece 14, as best shown in FIGS. 1, 9, 12 and 13; such a temperature-detection piece comprises in its interior a heat sensor 15 that is sensitive to IR radiation and is so arranged as to face outwardly, in particular so as to be directed towards a zone lying in front of the probing head 2. A manner in which this temperature-detection piece operates can at this point be readily understood: for a vegetable or fruit product to be measured, the product itself must be arranged in front of and in contact with the probing head 2, in such a manner as to be able to receive and re-emit radiation that is emitted by the LEDs, as described above.

In such a position, the product finds itself in an ideal situation in view of an outer temperature thereof being able to be detected automatically by the heat sensor 15, which is situated in direct view thereof. This so detected temperature value is then sent by the sensor to the PC unit for further processing, as described above.

In connection with this temperature-detection piece 14, a further improvement thereof appears to be anyway quite desirable: since vegetable products to be analyzed may be of species that differ to quite a large extent from each other, thereby possibly implying also largely differing sizes, the temperature-detection piece 14, if provided in a fixed position, could give rise to a twofold kind of a drawback. Namely, a first drawback would derive from the fact that the temperature-detection piece 14 might well interfere with undersized vegetable products, thereby preventing them from being able to be positioned directly in front of and in contact with the LEDs and in front of the outer surface 10 of an optical fiber, and this would clearly affect accuracy of measurements to be performed; a second drawback would on the other hand derive from the fact that the heat sensor 15, owing exactly to fixedness of its position regardless of a size of a vegetable product, would of course find itself positioned each time at very differing distances from a peel of the product, so that a so detected temperature shows and generates absolutely non-allowable margins of error.

Figure 12:
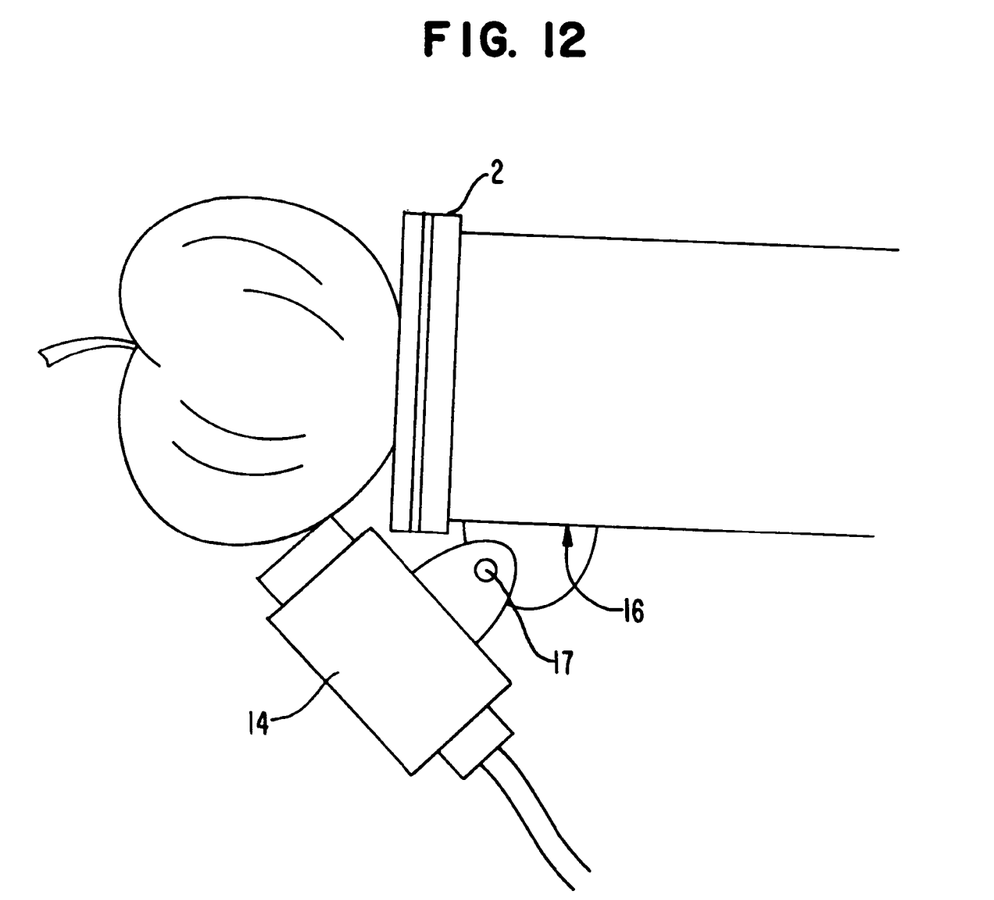
FIGS. 12 and 13 are the same view as the one shown in FIG. 9, with addition of variously sized vegetable or fruit products as arranged in respective measurement positions relative to the measuring instrument according to the present invention.
Figure 13:
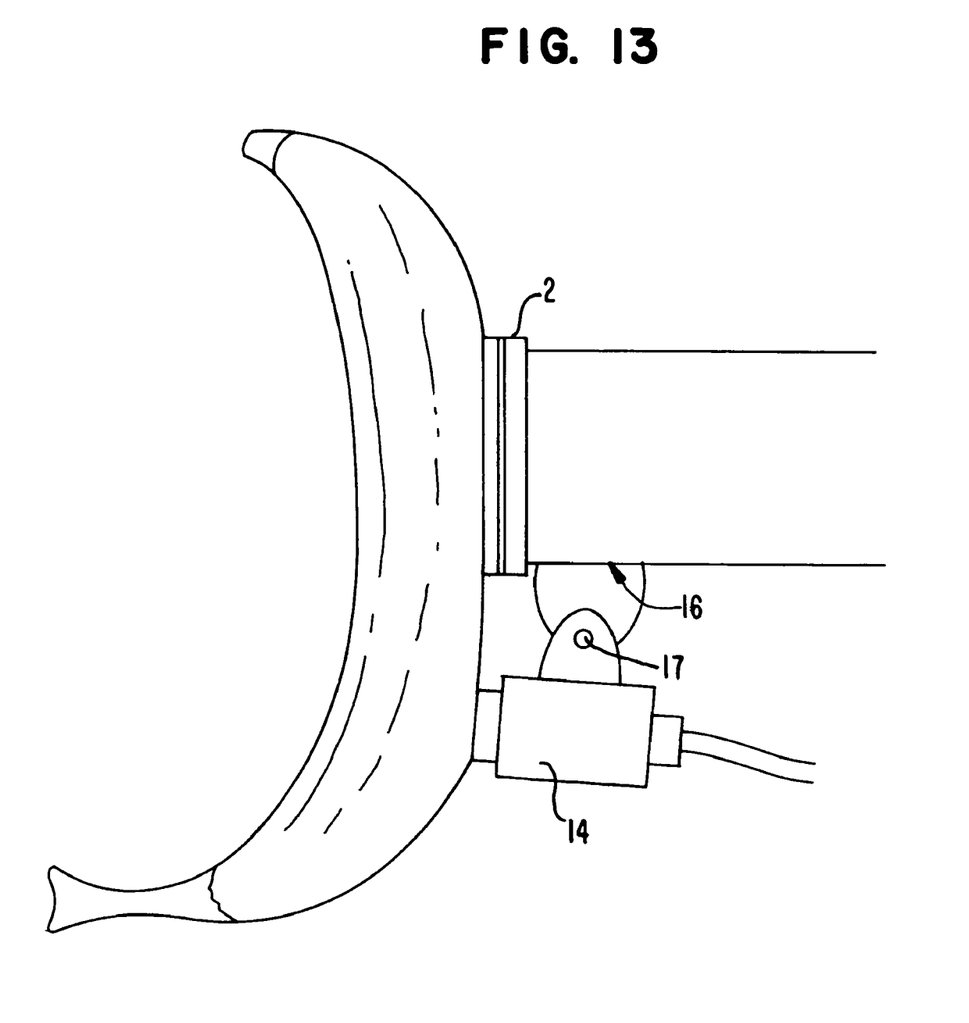

In view of doing away with such a major drawback, the temperature-detection piece 14 is therefore applied in an adjustable manner on an outer edge of the probing head 2 and, in particular, is connected pivotally on an outer edge 16 of the head 2 by pin-assisted hinging, i.e. by virtue of a hinging pin 17, as this is best shown in FIGS. 12 and 13 illustrating a self-adapting property of the temperature-detection piece 14 in accordance with varying sizes of vegetable products to be measured.

Furthermore, in order to enable operations for analysis of properties of vegetable or fruit products to be performed in as quick and convenient manner as possible, it is advantageous that, upon energization of the LEDs, phases of activation of the spectrometer, detection of the return or feedback radiation, processing of obtained values, presentation of these processed values and possible further statistical processing steps, as well as activation of possibly provided peripheral equipment, are switched on through a single activation switch 18, and that such a switch 18 is located in an expedient position on the handgrip 1.

Finally, in order to ensure full transportability of this measuring instrument, it is advantageous for the spectrometer, the processing and computation device, as well as remaining peripheral equipment to be integrated into a single casing 26 that is suitably equipped in view of being able to be conveniently transported by a single operator, as shown in FIG. 1.

The invention claimed is:

1. Apparatus for non-destructive measurement of internal properties of individual vegetable or fruit products, comprising:
    LEDs constructed and arranged to emit radiation into a vegetable or fruit product;
    pick-up structure constructed and arranged to pick up radiation, emitted by said LEDs, that has entered the vegetable or fruit product and then exited the vegetable or fruit product;
    a hollow cylinder between said LEDs and said pick-up structure for preventing radiation emitted by said LEDs from directly reaching said pick-up structure;
    a terminal ring adapted to be brought into abutment with the vegetable or fruit product;
    a spectrometer;
    structure for conveying to said spectrometer the radiation picked up by said pick-up structure; and
    structure for processing a spectrum frequency and amplitude data as produced by said spectrometer upon the radiation picked up by said pick-up structure being analyzed by said spectrometer,
    wherein said LEDs are contained in a portable casing including a handgrip and a probing head constructed and arranged to be brought into close proximity of, or into contact with, the vegetable or fruit product,
    wherein said spectrometer and said structure for processing are physically separated from said portable casing, and are electrically connected to said portable casing via an electrical conductor, and
    wherein said hollow cylinder projects from said probing head beyond terminal borders of said LEDs and said pick-up structure.

2. The apparatus according to claim 1, wherein
said terminal ring is coupled to an end portion of said hollow cylinder.

3. The apparatus according to claim 2, wherein
said structure for conveying radiation to said spectrometer is at least partially contained in said handgrip and said probing head.

4. The apparatus according to claim 1, wherein
said structure for conveying radiation to said spectrometer is at least partially contained in said handgrip and said probing head.

5. The apparatus according to claim 4, wherein
said LEDs are arranged according to a closed-loop ring pattern on a prominent surface of said probing head, and
said pick-up structure is arranged substantially at a center of said LEDs.

6. The apparatus according to claim 5, wherein
said pick-up structure includes a termination of an optical fiber.

7. The apparatus according to claim 1, wherein
said LEDs are to emit radiations, respectively, with emission spectra corresponding respectively to the radiations being substantially contiguous.

8. The apparatus according to claim 1, further comprising:
a temperature-detection piece, having a heat sensor, on an edge of said probing head.

9. The apparatus according to claim 8, wherein
said temperature-detection piece is pivotal with respect to said probing head via a hinging pin firmly joined to said probing head.

10. The apparatus according to claim 1, further comprising:
    a single activation switch that is to be triggered for activating said spectrometer and said structure for processing.

11. The apparatus according to claim 10, wherein
said single activation switch is on said handgrip.

12. The apparatus according to claim 1, wherein
said spectrometer and said structure for processing are assembled and integrated into a single portable casing.

13. The apparatus according to claim 12, wherein
said structure for processing is constructed and arranged to go through previously programmed algorithms, and solve previously programmed formulae, on a basis of previously entered constants and quantities as detected by said spectrometer, so as to obtain a plurality of values, each one of which is correlated in a univocal manner with at least one of the following parameters:
    (i) sugar contents (Brix degree),
    (ii) hardness,
    (iii) degree of ripeness,
    (iv) acidity, and
    (v) residual pesticides.

14. The apparatus according to claim 13, wherein
said structure for processing comprises a visualization display constructed and arranged to display a combination including at least one or more of the parameters.

15. The apparatus according to claim 14, wherein
said visualization display includes a field constructed and arranged to display a result of statistical processing of a plurality of measurements performed in connection with at least one of the parameters.

16. The apparatus according to claim 1, wherein
said structure for processing includes at least a disk-drive unit and a printer.

17. The apparatus according to claim 1, wherein
said terminal borders of said LEDs are positioned beyond said terminal border of said pick-up structure.

* * * * *